US012797546B2

(12) United States Patent
Alexandersson

(10) Patent No.: US 12,797,546 B2
(45) Date of Patent: Nov. 17, 2026

(54) SUB-ASSEMBLY FOR A MEDICAMENT DELIVERY DEVICE

(71) Applicant: SHL Medical AG, Zug (CH)

(72) Inventor: Oscar Alexandersson, Nacka Strand (SE)

(73) Assignee: SHL Medical AG, Zug (CH)

( * ) Notice: Subject to any disclaimer, the term of this patent is extended or adjusted under 35 U.S.C. 154(b) by 386 days.

(21) Appl. No.: 18/700,363

(22) PCT Filed: Sep. 30, 2022

(86) PCT No.: PCT/EP2022/077253
§ 371 (c)(1),
(2) Date: Apr. 11, 2024

(87) PCT Pub. No.: WO2023/061769
PCT Pub. Date: Apr. 20, 2023

(65) Prior Publication Data

US 2024/0408310 A1 Dec. 12, 2024

Related U.S. Application Data

(60) Provisional application No. 63/305,325, filed on Feb. 1, 2022.

(30) Foreign Application Priority Data

Oct. 14, 2021 (EP) .................................... 21202765

(51) Int. Cl.
*A61M 5/20* (2006.01)
*A61M 5/32* (2006.01)

(52) U.S. Cl.
CPC ........ *A61M 5/2033* (2013.01); *A61M 5/3245* (2013.01); *A61M 2005/2013* (2013.01);
(Continued)

(58) Field of Classification Search
CPC .............. A61M 5/2033; A61M 5/3245; A61M 2005/2013; A61M 2005/2073; A61M 2005/3267
See application file for complete search history.

(56) References Cited

U.S. PATENT DOCUMENTS 9,186,462 B2 11/2015 Lanzi
10,960,143 B2 3/2021 Hommann
(Continued)

FOREIGN PATENT DOCUMENTS

AU 2010303987 B2 4/2011
CN 113209421 A 8/2021
(Continued)

OTHER PUBLICATIONS

International Search Report and Written Opinion for corresponding PCT application No. PCT/EP2022/077253 dated Jan. 9, 2023.
Japanese Patent Office, Japanese Office Action for corresponding Japanese application No. 2024-522355 dated Dec. 27, 2024.

*Primary Examiner* — Dung T Ulsh
(74) *Attorney, Agent, or Firm* — McDonnell Boehnen Hulbert & Berghoff LLP

(57) ABSTRACT

The present disclosure provides a sub-assembly for a medicament delivery device configured to expel medicament from a medicament container via a delivery member. The sub-assembly includes (i) a housing having a proximal end and a distal end, (ii) a holding sleeve biased towards the proximal end of the housing, the holding sleeve including a locking member, (iii) a pre-tensioned plunger rod operably arranged to, upon activation, act on the medicament container for expelling a medicament, and (iv) an actuator having an arm arranged to lock the plunger rod in its pre-tensioned state, the actuator being operatively arranged to, upon activation, move the arm to release the plunger rod. The holding sleeve is operatively configured to be moved
(Continued)

proximally during a lockout operation in which the holding sleeve is axially locked by the locking member.

11 Claims, 5 Drawing Sheets

(52) U.S. Cl.
CPC ............... *A61M 2005/2073* (2013.01); *A61M 2005/3267* (2013.01)

(56) References Cited

U.S. PATENT DOCUMENTS

| | | | | |
|---|---|---|---|---|
| 2013/0296794 | A1 | 11/2013 | Brereton | |
| 2016/0089503 | A1* | 3/2016 | Olson | A61M 5/326<br>604/506 |
| 2018/0161504 | A1 | 6/2018 | Kemp | |
| 2018/0169338 | A1 | 6/2018 | Mosebach | |
| 2018/0353705 | A1* | 12/2018 | André | A61M 5/3157 |
| 2020/0197618 | A1* | 6/2020 | Holmqvist | A61M 5/2033 |
| 2020/0289754 | A1* | 9/2020 | Liscio | A61M 5/3158 |
| 2021/0154407 | A1 | 5/2021 | Hirschel | |

FOREIGN PATENT DOCUMENTS

| | | | |
|---|---|---|---|
| CN | 112076364 | B | 5/2024 |
| EP | 2170434 | B1 | 5/2012 |
| EP | 2203204 | B1 | 12/2014 |
| EP | 2745866 | B1 | 10/2016 |
| JP | 2018537251 | A | 12/2018 |
| JP | 2020527437 | A | 9/2020 |
| WO | 2008113864 | A1 | 9/2008 |
| WO | 2010136078 | A1 | 12/2010 |
| WO | 2013016832 | A1 | 2/2013 |
| WO | 2016193343 | A1 | 12/2016 |
| WO | 2016193355 | A1 | 12/2016 |
| WO | 2019086372 | A1 | 5/2019 |
| WO | 2022077910 | A1 | 4/2022 |

* cited by examiner

SUB-ASSEMBLY FOR A MEDICAMENT DELIVERY DEVICE

CROSS-REFERENCE TO RELATED APPLICATIONS

The present application is a U.S. National Phase Application pursuant to 35 U.S.C. § 371 of International Application No. PCT/EP2022/077253 filed Sep. 30, 2022, which claims priority to (i) European Patent Application No. 21202765.0 filed Oct. 14, 2021, and (ii) U.S. Provisional Application No. 63/305,325 filed Feb. 1, 2022. The entire disclosure contents of these applications are herewith incorporated by reference into the present application.

TECHNICAL FIELD

The present disclosure generally relates to a medicament delivery device for expelling medicament from a flexible medicament container. In particular, the present disclosure relates to a sub-assembly for a medicament delivery device.

BACKGROUND

A number of medical conditions require reliable provision of a medicament from a medicament delivery device. The medicament is typically comprised in a medicament container within the medicament delivery device, the medicament container being configured to expel the medicament via some type of delivery member, such as a needle or a nozzle.

These days, a number of different medicament delivery devices exist, including various types of injectors (for example pen injectors, autoinjectors, on-body devices). Although many of these devices have enabled major improvements in the management of a number of medical conditions, various drawbacks do still exist in the current technology.

Many medicament delivery devices comprise components which are movable relative each other. One type of relative movement between components may activate the medicament delivery device, e.g. exposing the delivery member or initiating expel of medicament from the medicament delivery device. Another type of relative movement between components may result in that two components are secured relative each other, e.g. by axially or radially fixating one component to another, or by means of a locking element. The relative fixation of components to avoid relative movement is often desired subsequent to using the medicament delivery device. That is, in the final state of the medicament delivery device, relative movement between components are undesired, as such relative movement may result in an unintentional actions of the medicament delivery device. Such unintentional actions may e.g. be the result of unsatisfactory relative fixation of components. In considering these problems, the applicant has appreciated that various developments could be made to help improve the medicament delivery devices on the market today, which are set out in more detail below.

SUMMARY

An object of the present disclosure is thus to provide a medicament delivery device which solves, or at least mitigates, problems of the prior art.

There is hence according to a first aspect of the present disclosure provide a sub-assembly for a medicament delivery device configured to expel medicament from a medicament container via a delivery member, the sub-assembly comprising: a housing having a proximal end and a distal end; a holding sleeve biased towards the proximal end of the housing, the holding sleeve a pre-tensioned plunger rod operably arranged to, upon comprising a locking member; activation, act on the medicament container for expelling a medicament; an actuator having an arm arranged to lock the plunger rod in its pre-tensioned state, the actuator being operatively arranged to, upon activation, move the arm to release the plunger rod; wherein the holding sleeve comprises a surface arranged to abut the arm of the actuator to lock the plunger rod in its pre-tensioned state by restricting movement of the arm of the activator, wherein the holding sleeve is operatively configured to move distally during a medicament delivery operation, thereby allowing the arm of the actuator to be released past an end portion of the holding sleeve causing said release of the plunger rod, and wherein the holding sleeve is operatively configured to be moved proximally during a lockout operation in which the holding sleeve is axially locked by the locking member.

An effect obtainable thereby is an improved lockout of the holding sleeve. That is, after use, the holding sleeve is arranged in a final state in which it is axially locked. Thus, the holding sleeve cannot move axially subsequent to the lockout operation. As the holding sleeve is axially locked, it obstructs movement of other components which are directly linked to the axial movement of the holding sleeve.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the components thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially" refer to a circumference or a circumferential direction relative to an axis, typically a central axis extending in the direction of the longest extension of the device and/or component. Similarly, "radial" or "radially" refer to a direction extending radially relative to the axis, and "rotation", "rotational" and "rotationally" refer to rotation relative to the axis.

According to one embodiment the sub-assembly further comprising a lockout structure, the lockout structure is arranged to interact with the locking member in a locking engagement to axially lock the holding sleeve. Hereby, the locking member of the holding sleeve may lockingly engage with the lockout structure to axially lock the holding sleeve.

Preferably, the lockout structure is arranged in a component or structure of the sub-assembly different to the holding sleeve.

According to one embodiment, the lockout structure is comprised in the actuator or the housing. The holding sleeve is typically arranged in between the housing and the actuator, such that the holding sleeve is arranged radially inwards of the housing, and radially outwards of the actuator, or the arm of the actuator. Thus, by arranging the lockout structure in one of the housing and the actuator, the axially locking of the holding sleeve if facilitated. That is, as the actuator and housing are arranged adjacent the holding sleeve, the locking member and the lockout structure will be arranged in components of the sub-assembly which are adjacent each other. Thus, as the holding sleeve moves axially within the housing in the proximal direction, i.e. moving axially relative to the housing and/or the actuator, the locking member is brought into engagement with the lockout structure to axially lock the holding sleeve.

According to one embodiment the locking member is arranged on a portion of the holding sleeve facing the actuator. Thus, preferably, the lockout structure is comprised in the actuator, such as on a portion of the actuator facing the holding sleeve. Hereby, the locking member may be brought into engagement with the lockout structure to axially lock the holding sleeve in a reliant manner. The portion of the holding sleeve facing the actuator may be referred to as an inner facing portion facing a centre axis of the sub-assembly, and the portion of the actuator facing the holding sleeve may be referred to as an outer facing portion facing away from a centre axis of the sub-assembly.

According to one embodiment, the locking member is an axial rib. Hereby, a simple yet effective structure for providing the locking functionality is provided. The axial rib has an extension in the axial direction, and an extension in the radial direction, wherein the extension in the axial direction is larger than the extension in the radial direction. For example, the axial rib extends axially along the portion of the holding sleeve facing the actuator, and extends radially towards the actuator.

According to one embodiment, the arm of the actuator comprises an end hook having a first hook portion arranged to lock the plunger rod in its pre-tensioned state, and a second hook portion arranged opposite to the first hook portion, the second hook portion forming the lockout structure and being arranged to interact with the locking member to axially lock the holding sleeve. Hereby, reliable structure for providing the lockout functionality is provided. Moreover, by comprising the locking structure in the arm of the actuator, the arm of the actuator serve a dual purpose, one being to lock the plunger rod in its pre-tensioned state, the other one being to lockingly engage with the locking member of the holding sleeve to axially lock the holding sleeve during a lockout operation.

According to one embodiment, the locking member is arranged on a portion of the holding sleeve facing the housing. Thus, preferably, the lockout structure is comprised in the housing, such as on a portion of the housing facing the holding sleeve. Hereby, the locking member may be brought into engagement with the lockout structure to axially lock the holding sleeve in a reliant manner. The portion of the holding sleeve facing the housing may be referred to as an outer facing portion facing away from centre axis of the sub-assembly, and the portion of the housing facing the holding sleeve may be referred to as an inner facing portion facing toward a centre axis of the sub-assembly.

According to one embodiment, the housing comprises an opening forming the lockout structure, and is arranged to receive the locking member to axially lock the holding sleeve. Hereby, reliable structure for providing the lockout functionality is provided. The locking member is here preferably arranged as a locking protrusion or resilient tongue extending radially outwards from the portion of the holding sleeve facing the housing. Moreover, by comprising the locking structure in the housing, the housing serve a dual purpose, one being to house the components of the sub-assembly, the other one being to lockingly engage with the locking member of the holding sleeve to axially lock the holding sleeve during a lockout operation.

According to one embodiment, the locking member is operatively arranged to snap-fit into the opening of the housing. Hereby, a simple yet reliable lockout functionality is provided. For example, as previously described, the locking member is preferably arranged as a protrusion or resilient tongue extending radially outwards from the portion of the holding sleeve facing the housing. Upon axial movement of the holding sleeve in the proximal direction, the protrusion or resilient tongue is guided along an inner surface of the housing until the protrusion or resilient tongue encounters the opening the housing, whereby the protrusion or resilient tongue is snap-fitted into the opening of the housing. Hereby, the holding sleeve is axially locked.

According to one embodiment, the holding sleeve is biased towards the proximal end of the housing by means of a distal resilient member, and wherein the distal resilient member presses the holding sleeve against the actuator or housing via the locking member in the lockout operation. Thus, the biasing force in the proximal direction is transferred to the actuator or housing via the holding sleeve and the locking member and lockout structure.

According to one embodiment, the sub-assembly further comprises a drive spring biasing the plunger rod towards the proximal end of the housing. Hereby, the plunger rod may be axially fixed relative to the housing in a first axial position by means of the actuator and actuator arm, and may be released from the first axial position and moved axially inside the housing due to the biasing force from the drive spring, as the plunger rod is released from its first axial position.

According to one embodiment, the sub-assembly further comprises a delivery member cover arranged in the housing and extending proximally from the proximal end of the housing, the delivery member cover being configured to, during the medicament delivery operation, move linearly relative to the housing from a protracted position to a retracted position in which the delivery member cover is received further in the housing. Subsequent to such medicament delivery operation, the delivery member cover is configured to move axially in the proximal direction, to again be brought into the protracted position. Hereby, the delivery member is protected inside the delivery member cover.

According to one embodiment, in the retracted position of the delivery member cover, a proximal end of the delivery member cover is arranged closer to the proximal end of the housing compared to in the protracted position. For example, in the retracted position, the proximal end of the delivery member cover is distant from the proximal end of the housing by a first axial distance, which first axial distance is smaller than a second axial distance between the proximal end of the delivery member cover and the proximal end of the housing in the protracted position.

According to one embodiment, the holding sleeve is fixedly attached to the delivery member cover. Hereby, axial lockout of the delivery cover member is provided. For example, the holding sleeve is axially and rotationally fixed relative to the delivery member cover, and is thus axially movable together with the delivery member cover. The delivery member cover may be axially locked in its protracted position, subsequent to a medicament delivery operation, to safely protect the delivery member in the delivery member cover. That is, after use, the holding sleeve is arranged in a final state in which it is axially locked together with the delivery member cover. Thus, the holding sleeve and the delivery member cover cannot move axially subsequent to the lockout operation. As the delivery member cover is axially locked, the delivery member is prevented from again being exposed.

There is according to a second aspect of the present disclosure provided a medicament delivery device for expelling medicament from a medicament container via a delivery member, the medicament delivery device comprising a sub-assembly according to the first aspect of the present disclosure.

Effects and features of the second aspect of the invention are largely analogous to those described above in connection with the first aspect of the invention. Embodiments mentioned in relation to the first aspect of the invention are largely compatible with the second aspect of the invention.

Generally, all terms used in the claims are to be interpreted according to their ordinary meaning in the technical field, unless explicitly defined otherwise herein. All references to "a/an/the member, apparatus, component, means, etc." are to be interpreted openly as referring to at least one instance of the member, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like members throughout the description.

Figure 1:
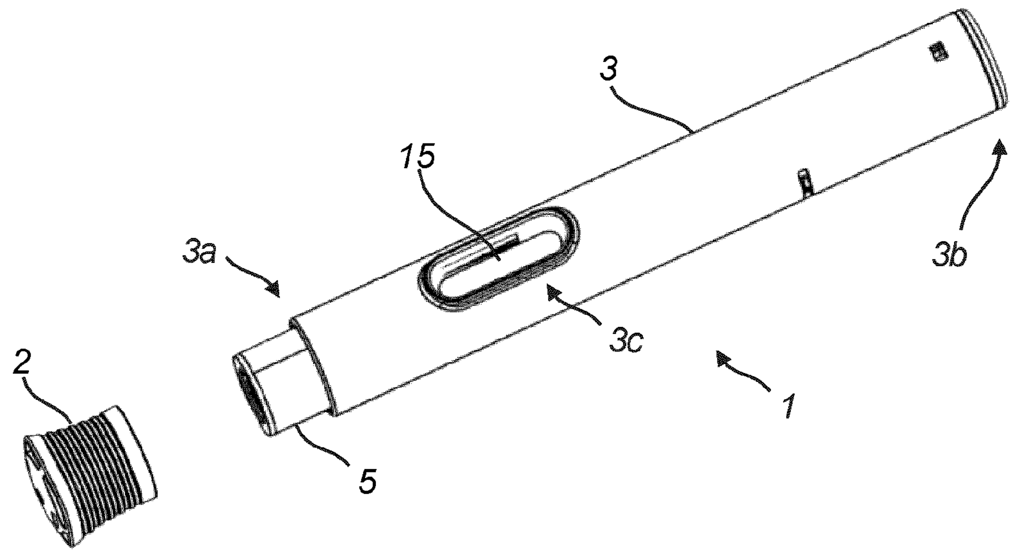
FIG. 1 schematically shows a perspective view of an example of a medicament delivery device.

FIG. 1 shows an example of a medicament delivery device 1 configured to expel medicament from a medicament container 15 loaded in a housing 3 of the medicament delivery device 1. The housing 3 has a proximal end 3*a* and a distal end 3*b*, and a window 3*c*, or opening, arranged between the proximal end 3*a* the distal end 3*b* for visual inspection of the medicament container 15.

The medicament delivery device 1 comprises a delivery member cover 5. The delivery member cover 5 is arranged in the housing 3 and extends proximally from the proximal end 3*a* of the housing 3. The medicament delivery device 1 further comprises a cap 2 removably arranged to the delivery member cover 5.

The delivery member cover 5 is configured to be moved linearly, or axially, relative to the housing 3 from a protracted position as shown in FIG. 1, into a retracted position in which the delivery member cover 5 is received further into the housing 3. Typically, the delivery member cover 5 is biased in the proximal direction towards the protracted position.

The medicament delivery device 1 is triggered to discharge medicament by movement of the delivery member cover 5 further into the housing 3 towards the retracted position.

Figure 2:
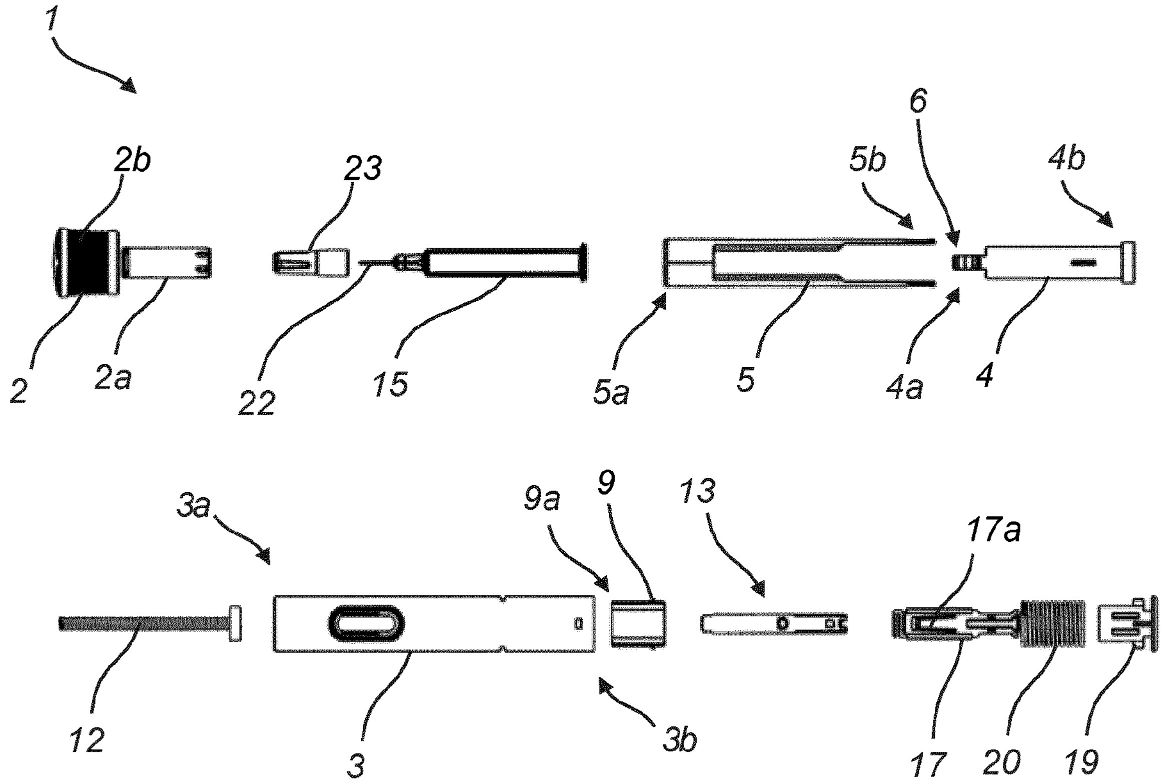
FIG. 2 shows an exploded view of the medicament delivery device in FIG. 1.

FIG. 2 shows an exploded view of the medicament delivery device 1. First, the general configuration of the medicament delivery device 1 will be described, then embodiments and certain aspects of various sub-assemblies 10, 11, 11' will be described in greater detail. The sub-assemblies of the medicament delivery device 1 may be defined by combining specific components of the medicament delivery device 1.

The medicament delivery device 1 comprises a medicament container carrier 4 extending along a longitudinal axis from a proximal end 4*a* to a distal end 4*b*. The medicament container carrier 4 may preferably be fixedly attached to the housing 3 of the medicament delivery device 1, e.g. by a snap lock or other conventional engagement means. Alternatively, the medicament container carrier 4 may form an integral part of the housing 3. The medicament container carrier 4 and the housing 3 are preferably made of the same material, e.g. plastic. The medicament container carrier 4 is configured to house and support the medicament container 15 inside the medicament delivery device 1. The medicament container carrier 4 further comprises an activation lock 6 which will be further explained with reference to FIGS. 3A-3C.

The medicament delivery device 1 comprises the delivery member cover 5 described with reference to FIG. 1. The delivery member cover 5 comprises a proximal end 5*a* and a distal end 5*b*. The activation lock 6 of the medicament container carrier 4 is preferably arranged between the proximal end 5*a* and the distal end 5*b* of the delivery member cover 5.

The medicament delivery device 1 comprises the cap 2 described with reference to FIG. 1. The cap 2 is removably arranged relative the delivery member cover 5. In the embodiment of FIG. 2, the cap 2 comprises a gripping portion 2*b* and a protrusion 2*a* extending in the longitudinal direction distally of the gripping portion 2*b*. The gripping portion 2*b* comprises a gripping surface which a user may interact with in order to remove the cap 2 from the delivery member cover 5. In FIG. 2, the protrusion 2*a* is a protruding sleeve 2*a*. The protruding sleeve 2*a* extends distally in the longitudinal direction.

The medicament delivery device 1 comprises a plunger rod 13 operably arranged to, upon activation, move in the proximal direction. Thus, in the embodiment of FIG. 2, the plunger rod 13 is configured to be moved axially inside the housing 3, and inside the medicament container carrier 4. During a medicament delivery operation, the plunger rod 13 moves from a first axial position towards the medicament container 15 for expelling the medicament. The plunger rod 13 may have a cylindrical body.

The medicament delivery device 1 comprises a drive spring 12 configured to bias the plunger rod 13 in the proximal direction. In the embodiment of FIG. 2, the plunger rod 13 is axially fixed relative to the medicament container carrier 4 and the housing 3 in the first axial position, when the delivery member cover 5 is in the protracted position prior to a medicament delivery operation.

The medicament delivery device 1 comprises an actuator 17 having an arm 17*a* arranged to lock the plunger rod 13 in a pre-tensioned state, and operatively arranged to, upon activation, move the arm 17*a* to release the plunger rod 13. In order to release the plunger rod 13, the distal end 5*b* of the delivery member cover 5 is arranged to engage with the actuator 17 to move the arm to release the plunger rod 13 as the delivery member cover 5 move axially into its retracted position. This will be further explained with reference to FIGS. 4A-4D.

The medicament delivery device 1 comprises a holding sleeve 9 arranged to move axially with the delivery member cover 5 inside of the housing 3. Thus, the holding sleeve 9 may be axially and rotationally fixed relative to the delivery member cover 5. When the delivery member cover 5 is moved from the protracted position towards the retracted position, linear movement of the delivery member cover 5 is transformed into linear movement of the holding sleeve 9. The holding sleeve 9 comprises a surface arranged to abut the arm 17*a* of the actuator 17 to lock the plunger rod 13 in its pre-tensioned state, wherein the holding sleeve 9 is operatively configured to move distally as the delivery member cover 5 is pushed into its retractive position causing the arm 17*a* of the actuator 17 to be released passed an end portion 9*a* of the holding sleeve 9 to release the plunger rod 13. This will be further explained with reference to FIGS. 4A-4D.

The medicament delivery device 1 comprises a distal resilient member 20. The distal resilient member 20 may for example be a spring, such as a coil spring. The distal resilient member 20 is configured to bias the delivery member cover 5 in the proximal direction. In the embodiment of FIG. 2, the distal resilient member 20 is configured to bias the delivery member cover 5 via the holding sleeve 9.

The medicament delivery device 1 comprises a rear end 19 arranged to close the housing 3 at the distal end 3*b* of the housing 3.

The medicament delivery device 1 can be loaded with a medicament container 15. The medicament container 15 typically comprises a delivery member 22, such as a needle 22, and a ring needle shield, RNS, 23 arranged to protect the delivery member 22. The medicament container 15 my further comprise an RNS needle cover and an RNS plastic cap (not shown). The protrusion 2*a* of the cap 2, may be referred to as an RNS remover, as it may be configured to remove the RNS 23 upon cap removal from the delivery member cover 5.

Figure 3A:
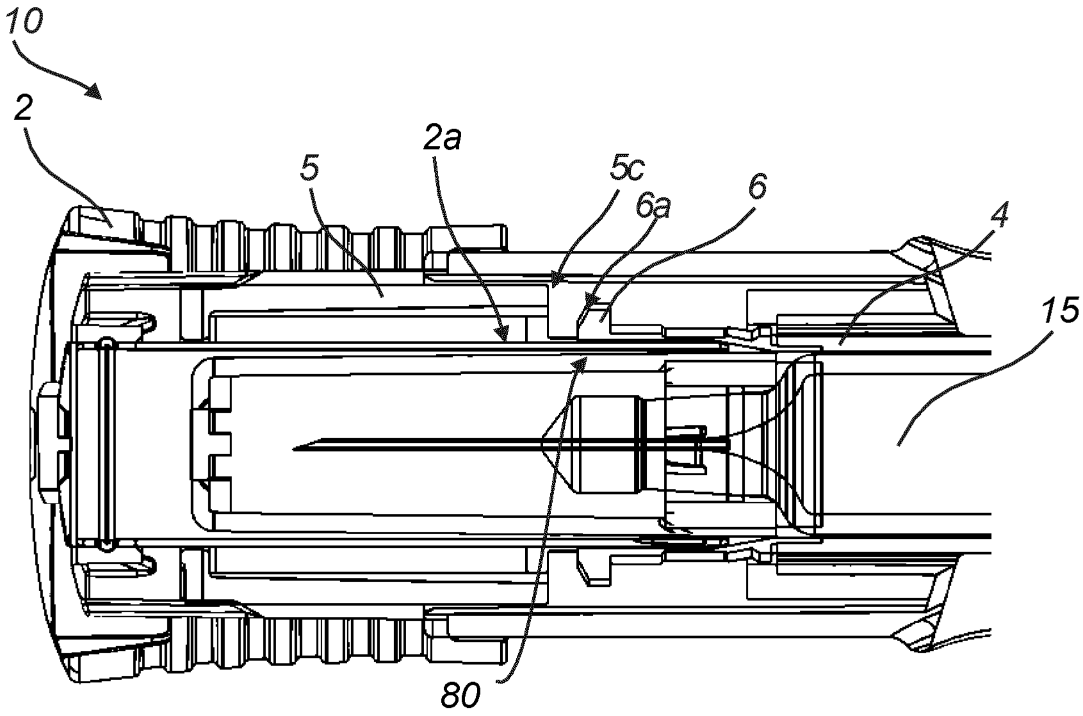
FIG. 3A is a detailed cross-sectional view of at least a part of a sub-assembly of the medicament delivery device FIG. 2, wherein the sub-assembly is in its pre-activation preventing state.

FIG. 3A shows a detailed cross-sectional view of at least a part of a sub-assembly 10 of the medicament delivery device 1 of FIG. 2. The sub-assembly 10 comprises at least the medicament container carrier 4, the delivery member cover 5 and the cap 2. In the detailed view of FIG. 3A, the activation lock 6 of the medicament container carrier 4 is shown adjacent to the protrusion 2*a*, or protruding sleeve 2*a*, of the cap 2. In FIG. 3A, the sub-assembly 10 is shown in a pre-activation preventing state in which the protrusion 2*a* is adjacent the activation lock 6 to prevent the activation lock 6 from moving radially inwards, and thereby preventing axial movement of the delivery member cover 5 into its retracted position. I more detail, a space 80 is arranged adjacent the activation lock 6, wherein, in the pre-activation preventing state shown in FIG. 3A, the protrusion 2*a* is arranged in that space 80, whereby any radially induced movement of the activation lock 6 will be stopped by the protrusion 2*a*. As shown in FIG. 3A, a distally facing surface 5*c* of the delivery member cover 5 is arranged to abut the activation lock 6 preventing axial movement of the delivery member cover 5 beyond the activation lock 6. The distally facing surface 5*c* is partly defining a sleeve portion of the delivery member cover 5, the distally facing surface 5*c* being arranged circumferentially of the sleeve portion. In more detail, the activation lock 6 comprises a proximally facing surface 6*a* aligned in the axial direction with the distally facing surface 5*c*. Due to the alignment of the proximally facing surface 6*a* and the distally facing surface 5*c*, axial movement of the delivery member cover 5 into its retracted position is prevented.

Figure 3B:
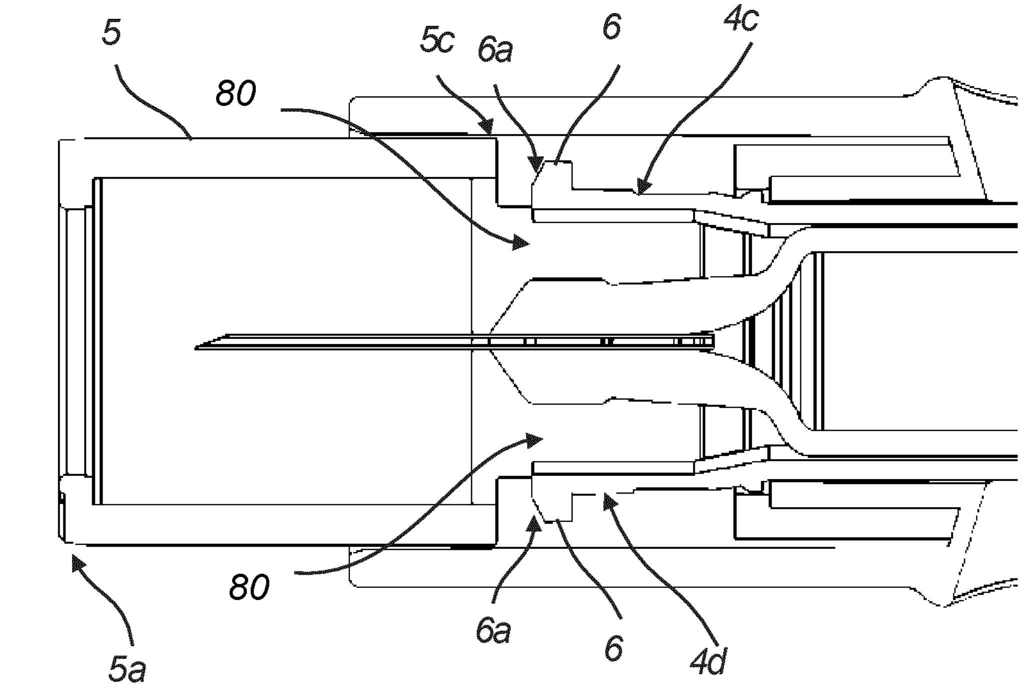
FIG. 3B shows the sub-assembly of FIG. 3A in its activation admittable state with the delivery member cover in its protracted position.
Figure 3C:
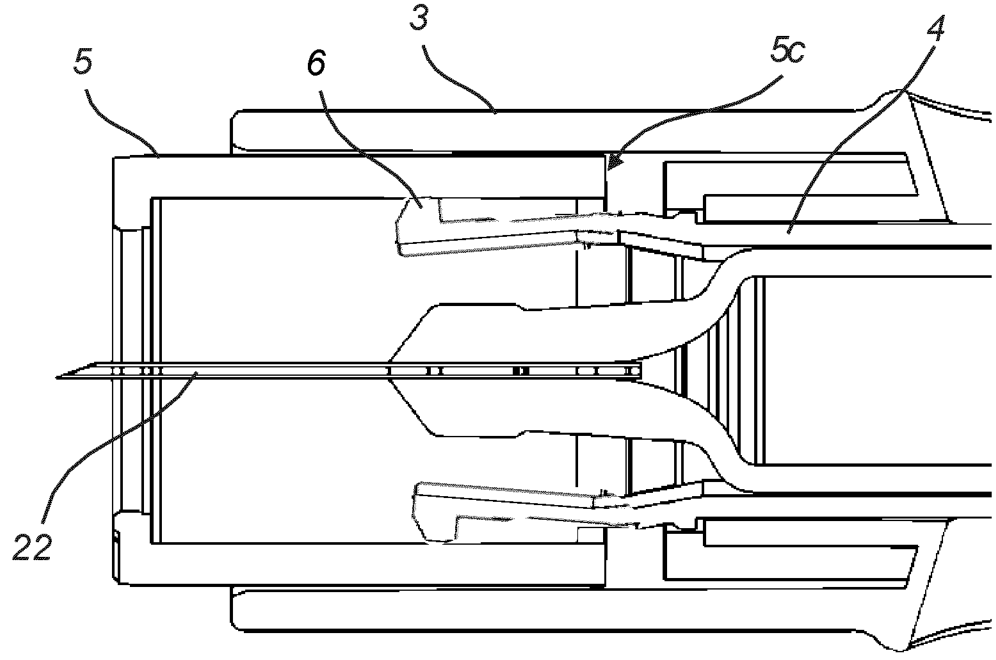
FIG. 3C shows the sub-assembly of FIG. 3A in a state in which the delivery member cover is arranged in its retracted position.

Turning to FIG. 3B showing the same detailed cross-sectional view of FIG. 3A, but for an activation admittible state in which the cap 2 is removed from the delivery member cover 5. Upon removal of the cap 2, the protrusion 2*a* is withdrawn from the space 80. Moreover, the RNS 23 has been removed from the medicament container 15 together with the protrusion 2*a*, to thereby uncover the delivery member 22. In FIG. 3B, the space 80 is configured to receive the activation lock 6. Thus, a radially induced force applied to the activation lock 6 will move the activation lock 6 radially inwards into the space 80, and thereby enable axial movement of the delivery member cover 5 into its retracted position (as shown in FIG. 3C). Thus, the sub-assembly 10 is movable from the pre-activation preventing state as shown in FIG. 3A, in which the protrusion 2*a* is adjacent the activation lock 6 to prevent the activation lock 6 from moving radially inwards, to an activation admittible state as shown in FIG. 3B, in which the activation lock 6 is allowed to move radially and thereby enabling axial movement of the delivery member cover 5 into its retracted position.

In more detail, the activation lock 6 is flexible and is configured to radially move by flexing inwards towards a centre axis of the sub-assembly 10. Preferably, the activation lock 6 forms part of the proximal end 4*a* of the medicament container structure 4. As shown in FIG. 3B, the activation lock 6 comprises two oppositely arranged longitudinal arms 4*c*, 4*d* extending proximally from a main portion of the medicament container carrier. Each one of the longitudinal arms 4*c*, 4*d* is configured with a corresponding proximally facing surface 6*a*, and is configured to radially move by flexing inwards towards a centre axis of the sub-assembly 10. The main portion of the medicament container carrier is configured to house a main body of the medicament container 15. Each one of the two oppositely arranged longitudinal arms 4*c*, 4*d* has an end portion that is flexibly arranged relative the space 80.

As shown in FIG. 3B, each one of the proximally facing surfaces 6*a* is at least partly chamfered. Hereby, the action of pushing the activation lock 6 into the space 80 is facilitated. That is, by that each one of the proximally facing surfaces 6*a* is at least partly chamfered, an externally applied force in the distal direction may be at least partly transformed into a radial force due to the interaction of the distally facing surface 5*c* with the proximally facing surfaces 6*a*. As shown in FIG. 3B, the proximally facing surfaces 6*a* is chamfered to be inclined away from the distally facing surface 5*c*.

Typically, the proximal end 5*a* of the delivery member cover 5 is subject to the externally applied force causing the delivery member cover 5 to move distally in the axial direction such that the distally facing surface 5*c* abuts the activation lock 6, and the proximally facing surfaces 6*a*, to push the activation lock 6 into the space 80. Thus, the applied force from the distally facing surface 5*c* forces the activation lock 6 to move radially inwards into the space 80. Thus, the distally facing surface 5*c* is able to move distally beyond the activation lock 6 and thereby enable the delivery member cover 5 to be moved into its retracted position. Such configuration is shown in FIG. 3C. In the retracted position of the delivery member cover 5, the delivery member 22 is exposed and ready for expelling the medicament. As shown in FIG. 3B-3C, the housing 3 is arranged outside of the medicament container carrier 4, and at least partly houses the delivery member cover 5. Thus, the delivery member cover 5 is furthermore configured to be moved linearly, or axially, relative to the housing 3 from the protracted position shown in FIG. 3B to the retracted position shown in FIG. 3C in which the delivery member cover 5 is received further in the housing 3.

The operation of the medicament delivery device 1 will now be described in more detail with reference to FIGS. 4A-D. Reference will be made primarily to the medicament delivery device 1, even though certain components thereof may belong to the sub-assembly 10 of the medicament delivery device 1 described with reference to FIG. 3A-3C, or may belong to any of the sub-assemblies 11, 11' described with reference to FIGS. 5A-5C.

Figure 4A:
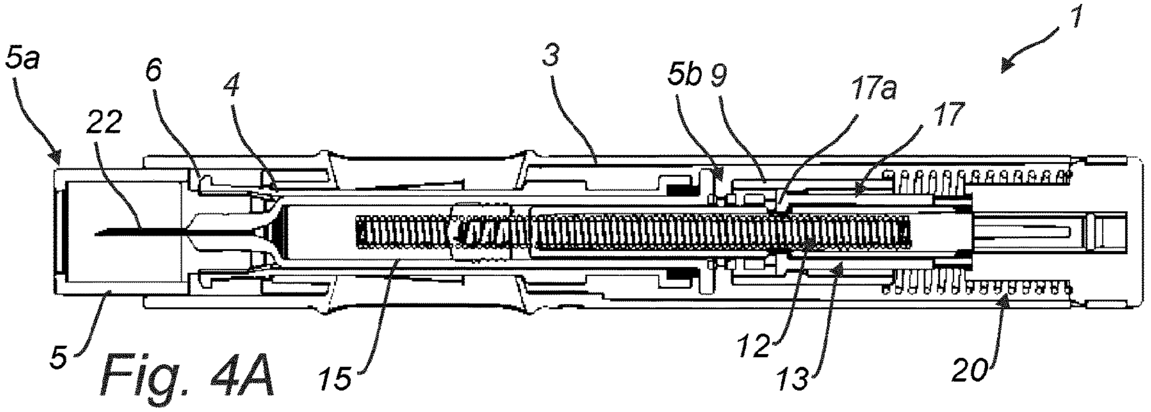
FIG. 4A is a sectional view of the medicament delivery device in a default state subsequent to removing the cap.

FIG. 4A shows a sectional view of the medicament delivery device 1 in a default state before medicament delivery, and subsequent to removing the cap 22. Thus, the sub-assembly 10 is arranged in its activation admittable state as described with reference to FIG. 3B.

The delivery member cover 5 is in the protracted position, biased in the proximal direction by the distal resilient member 20. The delivery member cover 5 is biased by the distal resilient member 20 via the holding sleeve 9. The delivery member cover 5 covers the delivery member 22 of the medicament container 15.

The plunger rod 13 is axially fixed relative to the medicament container carrier 4 and the housing 3 in the first axial position, and biased in the proximal direction by means of the drive spring 12.

Figure 4B:
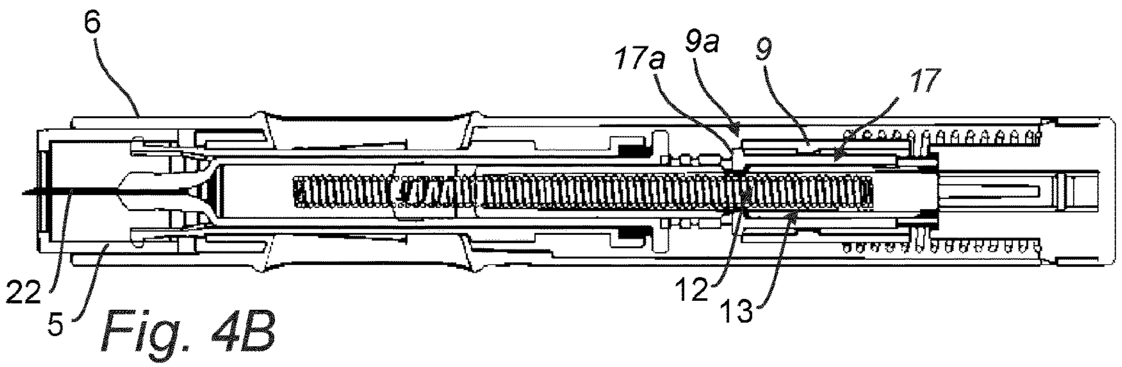
FIG. 4B is a sectional view of the medicament delivery device in an activated state, at the commence of a medicament delivery operation.

The actuator 17 is arranged such that the arm 17*a* lock the plunger rod 13 in the pre-tensioned state. As shown in FIG. 4B, the actuator 17 comprises two longitudinal extending arms 17*a*, 17*b*, hereafter referred to as actuator arms 17*a*, 17*b*, arranged opposite each other. The structure and function of the two actuator arms 17*a*, 17*b* are analogous, why only one of the actuator arms 17*a*, 17*b* occasionally is described. The actuator arms 17*a*, 17*b* are locked in position by the holding sleeve 9. As mentioned with reference to FIG. 2, a surface of the holding sleeve 9 is arranged to abut the actuator arms 17*a*, 17*b* to lock the plunger rod 13 in its pre-tensioned state. The holding sleeve 9 engages with the distal end 5*b* of the delivery member cover 5 such that the holding sleeve 9 is axially fixed, and movable with, the delivery member cover 5.

FIG. 4B shows a sectional view of the medicament delivery device 1 in an activated state, at the point in time of the release of the plunger rod 13. The medicament delivery device 1 is pressed against the site of injection by the operator. Thus, the resulting externally applied force has caused the delivery member cover 5 to be moved into its retracted position wherein the delivery member 22 is exposed for penetrating the tissue, as also shown in FIG. 3C. Thus, the proximal end 5*a* of the delivery member cover 5 has been subject to the externally applied force causing the delivery member cover 5 to move distally in the axial direction such that the distally facing surface 5*c* abuts the activation lock 6, and the proximally facing surfaces 6*a*, to push the activation lock 6 into the space 80, as described with reference to FIG. 3C. The holding sleeve 9 is axially fixed, and movable with, the delivery member cover 5, and as the delivery member cover 5 is moved into its retracted position, the holding sleeve 9 is moved distally causing the actuator arms 17*a*, 17*b* to be released passed an end portion 9*a* of the holding sleeve 9 to release the plunger rod 13.

Figure 4C:
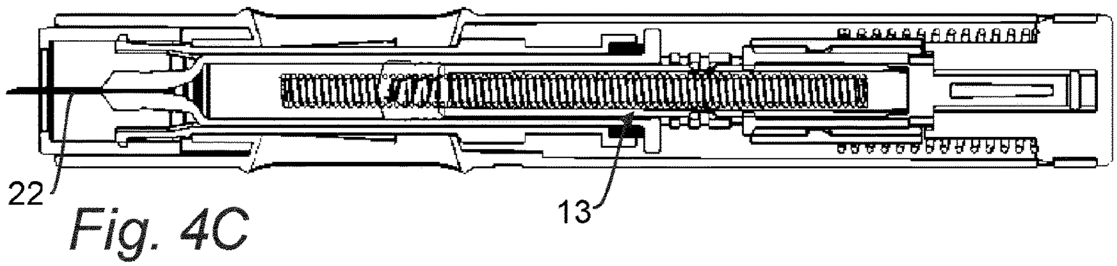
FIG. 4C is a sectional view of the medicament delivery device during a medicament delivery operation.

FIG. 4C shows the medicament delivery device 1 during a medicament delivery operation. The plunger rod 13 is released from its first axial position shown in FIG. 4B, and moves proximally towards the medicament container 15. Thus, the plunger rod 13 moves axially towards the proximal end 3*a* of the housing 3, and towards the proximal end 4*a* of the medicament container carrier 4, due to the biasing force from the drive spring 12. This proximal movement causes the plunger rod 13 to encounter the medicament container 15 for expelling medicament via the delivery member 22 by pushing the content of the medicament container through the delivery member 22.

Figure 4D:
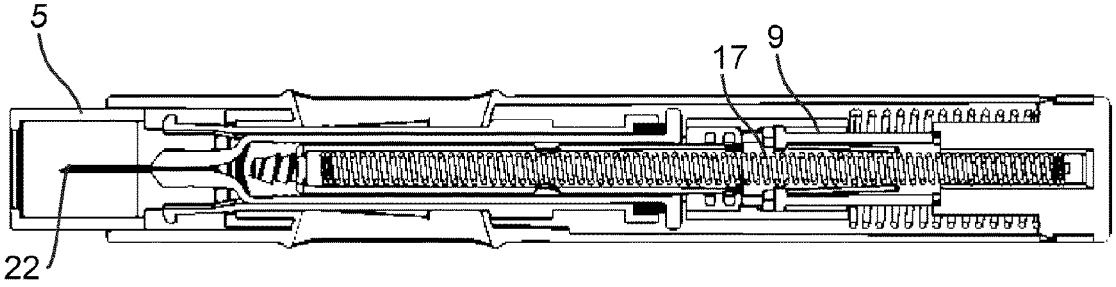
FIG. 4D is a sectional view of the medicament delivery device subsequent to the medicament delivery operation.

At the beginning of medicament expulsion, the plunger rod 13 is axially positioned adjacent the actuator arms 17*a*, 17*b*, and thus the actuator arms 17*a*, 17*b* withstand the radially inwards directed force applied by the holding sleeve 9 and the biasing force from the distal resilient member 20 provided onto the holding sleeve 9. Once the plunger rod 13 has moved further in the proximal direction, and content of the medicament container 15 has been discharged, the plunger rod 13 is no more axially positioned adjacent the actuator arms 17*a*, 17*b*, and the radially inwards directed force applied by the holding sleeve 9 and the biasing force from the distal resilient member 20, forces the actuator arms 17*a*, 17*b* radially inwards. Hereby the holding sleeve 9 can move in the proximal direction together with the delivery member cover 5 to achieve a lockout, as shown in FIG. 4D. Thus, FIG. 4D shows the medicament delivery device 1 when the actuator arms 17*a*, 17*b* have collapsed into the void left by the plunger rod 13 (also shown in FIG. 5B). As a result, the holding sleeve 9 is moved in the proximal direction by the biasing force from the distal resilient member 20. The delivery member 22 is again covered by the delivery cover member 5 which shows a final state of the medicament delivery device 1, after use. Thus, the delivery member cover 5 is again brought into its protracted position. The medicament delivery device 1 may be disposed of in this final state, in which the delivery member 22 is protected inside the delivery member cover 5. The delivery member cover 5 is axially locked in the protracted position by a locking member 30, 31 and a lockout structure 42, 50 as will be further described with reference to FIGS. 5A-5C.

Figure 5A:
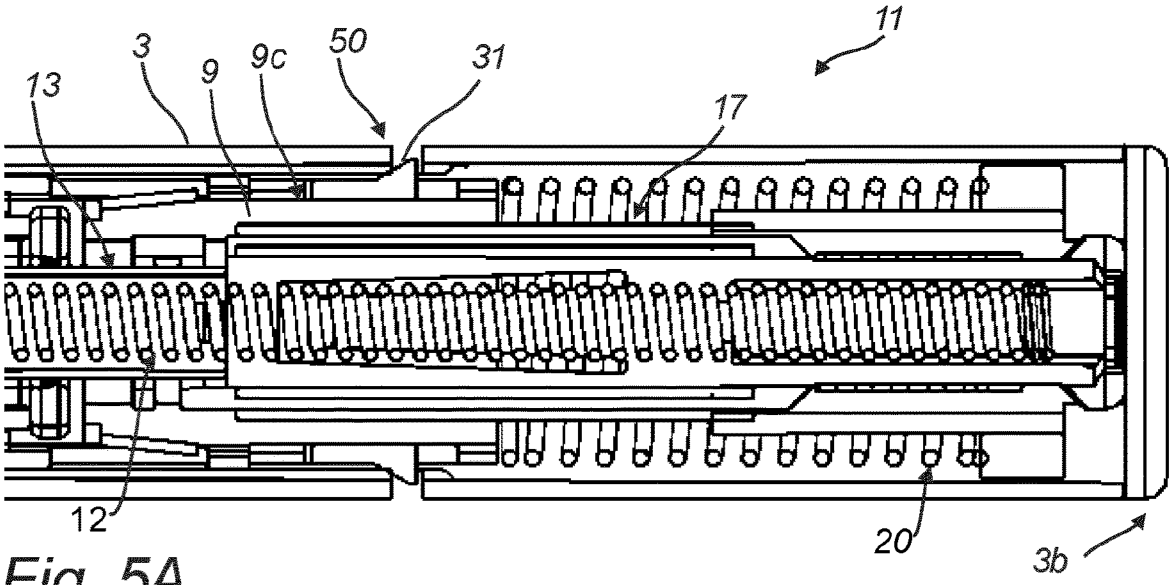
FIG. 5A is a detailed cross-sectional view of at least a part of another sub-assembly of the medicament delivery device of FIG. 2.
Figure 5B:
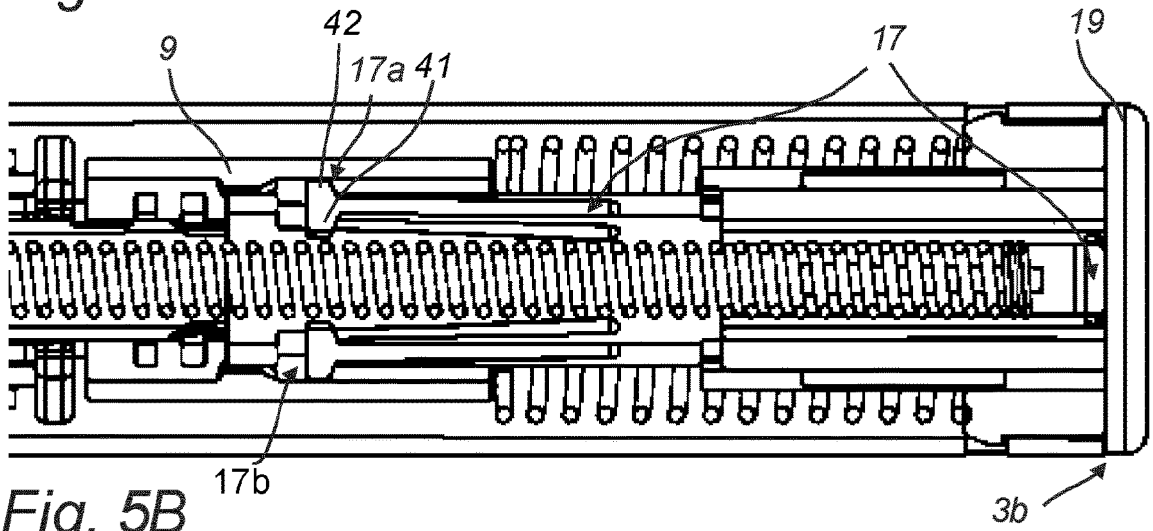
FIG. 5B shows a sectional view in a plane at 90 degrees angle relative to the sectional view shown in FIG. 5A.

FIG. 5A is a detailed cross-sectional view of at least a part of a sub-assembly 11 of the medicament delivery device 1 of FIG. 2. FIG. 5B shows a sectional view in a plane at 90 degrees angle relative to the sectional view shown in FIG. 5A. In FIGS. 5A and 5B, a final state of the medicament delivery device 1 is shown, i.e. after use, in which the medicament has been expelled from the medicament container, corresponding to the state shown in FIG. 4D.

The sub-assembly 11 comprises the housing 3 with the proximal end 3*a* and the distal end 3*b*, as previously described. In FIGS. 5A and 5B only a portion of the housing 3 including the distal end 3*b* is shown. The sub-assembly 11 further comprises the holding sleeve 9 proximally biased in housing 3. The holding sleeve 9 comprising a locking member 31 in the form of a locking protrusion 31 extending radially outwards from a portion 9*c* of the holding sleeve facing the housing 3.

The sub-assembly 11 comprises the actuator 17 with its actuator arms 17*a*, 17*b*, previously described and best shown in FIG. 5B. The sub-assembly 11 also comprises the plunger rod 13, which in FIGS. 5A and 5B has been moved proximally to interact with the medicament container (not shown). Thus, as the plunger rod 13 has moved further in the proximal direction, and any content of the medicament container 15 has been discharged, the plunger rod 13 is no more axially positioned adjacent the actuator arms 17*a*, 17*b* in FIG. 5B, and a radially inwards directed force applied by the holding sleeve 9 and the biasing force from the distal resilient member 20, forces the actuator arms 17*a*, 17*b* radially inwards. Hereby, the holding sleeve 9 can be arranged radially outwards of the actuator arms 17*a*, 17*b*. Moreover, as the support from the plunger rod 13 to the actuator arms 17*a*, 17*b* is removed, the actuator 17 is pushed towards the distal end 3*b* of the housing 3 by the drive spring 12. As the actuator 17 impacts the rear end 19 of the medicament delivery device 1, an audible and/or tactile feedback to the user is achieved.

Moreover, the sub-assembly 11 may comprise the drive spring 12 biasing the plunger rod 13 towards the proximal end 3*a* of the housing 3. Thus, in FIGS. 5A and 5B, the holding sleeve 9 has been moved proximally during a lockout operation in which the holding sleeve 9 is axially locked by the locking member 31, here in the form of the locking protrusion 31.

As shown in FIG. 5A, the housing 3 comprises a lockout structure 50 interacting with the locking protrusion 31 in a locking engagement to axially lock the holding sleeve 9. In more detail, the lockout structure 50 is formed by an opening 50 in the housing. The opening 50 is arranged to receive the locking protrusion 31 to axially lock the holding sleeve 9. That is, as the locking protrusion 31 is arranged on the portion 9*c* of the holding sleeve 9 facing the housing 3, the locking protrusion 31 may be brought into contact with the opening 50 during axial and proximal movement of the holding sleeve 9 during the lockout operation. Preferably, the locking protrusion 31 is snap-fitted into the opening 50.

Figure 5C:
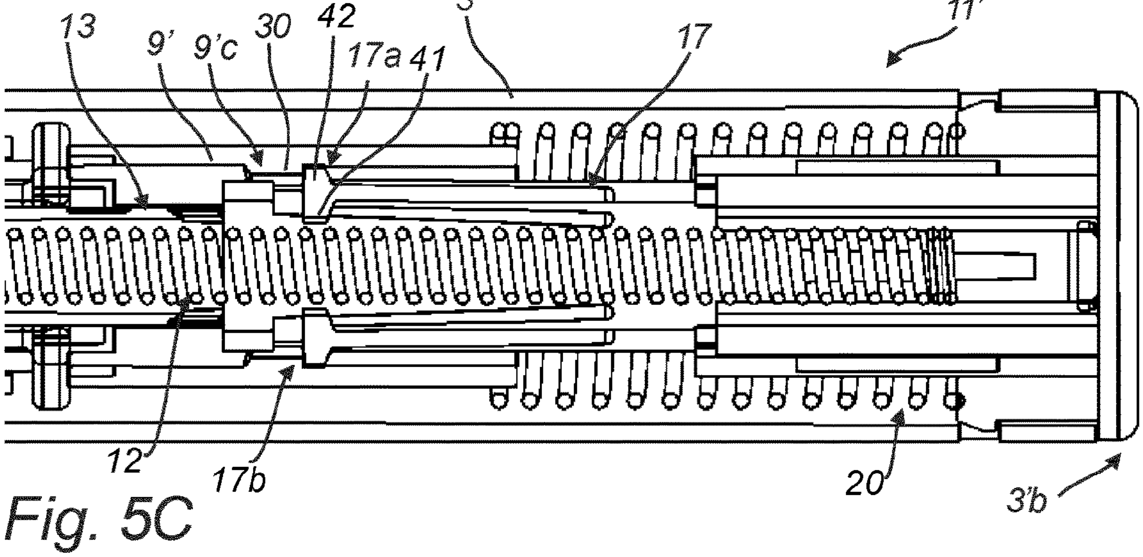
FIG. 5C is a detailed cross-sectional view of at least a part of yet another sub-assembly of a medicament delivery device.

FIG. 5C is a detailed cross-sectional view of at least a part of another sub-assembly 11' of a medicament delivery device. The sub-assembly 11' of FIG. 5C is in large corresponding to the sub-assembly 11 of FIGS. 5A and 5B, why primarily the differences are described below. Thus, the sub-assembly 11' may form a part of the medicament delivery device 1 of FIG. 2. For example, the actuator 17, the plunger rod 13 and optionally the drive spring 12 of the sub-assembly 11 of FIGS. 5A and 5B are comprise in the sub-assembly 11' of FIG. 5C. In FIG. 5C, a final state of the medicament delivery device is shown, i.e. after use, in which the medicament has been expelled from the medicament container, corresponding to the state shown in FIG. 4D.

The sub-assembly 11' comprises a housing 3' with proximal end 3'*a* and distal end, as previously described, except that the housing 3' does not comprise a corresponding opening 50 for interacting with a locking member 31 of the holding sleeve 9. The sub-assembly 11' further comprises a holding sleeve 9' proximally biased in housing 3'. The holding sleeve 9' is in large corresponding to the holding sleeve 9 of FIGS. 5A and 5B, but instead of comprising the locking member in a portion 9*c* facing the housing 3, the locking member 30 is arranged on a portion 9'*c* of the holding sleeve 9' facing the actuator 17. In FIG. 5C, the looking member 30 is formed by an axial rib 30. The axial rib extends in the axial direction and extends radially outwards of the portion 9'*c* of the holding sleeve 9'.

Each one of the actuator arms 17*a*, 17*b* comprises an end hook 40. As the end hook 40 is similar or corresponding for the two actuator arms 17*a*, 17*b*, it will only be described for a first actuator arm 17*a*. The end hook 40 comprises a first hook portion 41 configured to lock the plunger rod 13 in its pre-tensioned state (correspondingly that shown in FIG. 4A), and a second hook portion 42 arranged opposite to the first hook portion 41. The second hook portion 42 forms the lockout structure 42 and is thus configured to interact with the axial rib 30 to axially lock the holding sleeve 9'. The sub-assembly 11 may comprise the same actuator 17, with the first and second hook portions 41, 42, as shown in FIG. 5B.

As shown in FIGS. 5A-5C, the sub-assemblies 11, 11' may comprise the distal resilient member 20 previously described. The distal resilient member 20 is configured to press the corresponding holding sleeve 9, 9' against the actuator 17 (for the embodiment in FIG. 5C) or the housing 3 (for the embodiment in FIGS. 5A and 5B) via the locking member 30, 31.

Moreover, the sub-assemblies 11, 11' may comprise the delivery member cover 5 previously described. Thus, the corresponding holding sleeve 9, 9' may be fixedly attached to the delivery member cover 5, and thereby axially lock the delivery member cover 5 during the lockout operation.

The inventive concept has mainly been described above with reference to a few examples. However, as is readily appreciated by a person skilled in the art, other embodiments than the ones disclosed above are equally possible within the scope of the inventive concept, as defined by the appended claims. For example, the drive member could for example be motor driven or manually driven instead of having an automatic spring-loaded structure.

Some aspects are summarized in the following clauses.

1. A sub-assembly (10) for a medicament delivery device (1), the sub-assembly (10) comprising:

a medicament container carrier (4) extending along a longitudinal axis from a proximal end (4*a*) to a distal end (4*b*), the medicament container carrier (4) comprising an activation lock (6);

a delivery member cover (5) arranged at least partly proximal of the medicament container carrier (4), the delivery member cover (5) being configured to move axially relative to the medicament container carrier (4) from a protracted position to a retracted position;

a cap (2) removably arranged at least partly proximal the delivery member cover (5), the cap (2) comprising a protrusion (2*a*);

wherein the sub-assembly (10) is configured to move from: a pre-activation preventing state in which the protrusion (2*a*) is adjacent the activation lock (6) to prevent the activation lock from moving radially and thereby preventing axial movement of the delivery member cover (5) into its retracted position; into an activation admittible state in which the cap is removed to distance the protrusion (2*a*) from the activation lock (6) to allow the activation lock (6) to move radially and thereby enabling axial movement of the delivery member cover (5) into its retracted position.

2. The sub-assembly (10) according to clause 1, wherein the delivery member cover (5) comprises a distally facing surface (5*c*), and wherein the activation lock (6) comprises a proximally facing surface (6*a*) aligned in the axial direction with the distally facing surface (5*c*) to prevent axial movement of the delivery member cover (5) into its retracted position in the pre-activation preventing state.

3. The sub-assembly (10) according to any one of the preceding clauses, wherein the activation lock (6) is flexible, and wherein, in the activation admittible state, the activation lock (6) is configured to radially move by flexing inwards towards a centre axis of the sub-assembly (10).

4. The sub-assembly (10) according to any one of the preceding clauses, further comprising a space (80) adjacent the activation lock (6), wherein, in the pre-activation preventing state, the protrusion (2*a*) is arranged in said space (80).

5. The sub-assembly (10) according to clause 4, wherein, in the activation admittible state, said space (80) is arranged to receive the activation lock (6) to achieve said activation admittible state.

6. The sub-assembly (10) according to clauses 2 and 5, wherein the delivery member cover (5) is configured to, upon an externally applied force in the distal direction, bring the distally facing surface (5*c*) to abut the proximally facing surface (6*a*) and thereby push the activation lock (6) into said space (80).

7. The sub-assembly (10) according to clause 6, wherein the proximally facing surface (6*a*) is at least partly chamfered.

8. The sub-assembly (10) according to any one of the preceding clauses, wherein the medicament container carrier and the activation lock (6) form part of a housing (3) of the medicament delivery device.

9. The sub-assembly (10) according to any one of the preceding clauses, further comprising a plunger rod (13) operably arranged to, upon activation, move towards the proximal end (4*a*) of the medicament container carrier (4).

10. The sub-assembly (10) according to clause 9, further comprising an actuator (17) having an arm arranged to lock the plunger rod (13) in a pre-tensioned state, and operatively arranged to, upon activation, move the arm to release the plunger rod (13).

11. The sub-assembly (10) according to any one of the preceding clauses, wherein the delivery member cover (5) comprises a proximal end (5*a*) and a distal end (5*b*), and wherein the activation lock (6) is arranged between the proximal end (5*a*) and the distal end (5*b*) of the delivery member cover (5).

12. The sub-assembly (10) according to clauses 10-11, wherein the distal end (5*b*) of the delivery member cover (5) is arranged to engage with the actuator (17) to move the arm to release the plunger rod (13) as the delivery member cover (5) move axially into its retracted position.

13. The sub-assembly (10) according to clause 12, further comprising a holding sleeve (9) arranged to move axially with the delivery member cover (5), wherein the holding sleeve (9) comprises a surface arranged to abut the arm of the actuator (17) to lock the plunger rod (13) in its pre-tensioned state, wherein the holding sleeve is operatively configured to move distally as the delivery member cover (5) is pushed into its retractive position causing the arm of the actuator (17) to be released passed an end portion (9*a*) of the holding sleeve (9) to release the plunger rod (13).

14. A medicament delivery device (1) configured to expel medicament from a medicament container (15) via a delivery member (22), the medicament delivery device (1) comprising a sub-assembly (10) according to any one of clauses 1-13.

The invention claimed is:

1. A sub-assembly for a medicament delivery device configured to expel medicament from a medicament container via a delivery member, the sub-assembly comprising:

a housing having a proximal end and a distal end;

a holding sleeve biased towards the proximal end of the housing, the holding sleeve comprising a locking member;

a pre-tensioned plunger rod operably arranged to, upon activation, act on the medicament container for expelling a medicament; and an actuator having an arm arranged to lock the plunger rod in its pre-tensioned state, the actuator being operatively arranged to, upon activation, move the arm to release the plunger rod; and a lockout structure, the lockout structure being arranged to interact with the locking member in a locking engagement to axially lock the holding sleeve, wherein the housing comprises an opening forming the lockout structure and being arranged to receive the locking member to axially lock the holding sleeve, wherein the holding sleeve comprises a surface arranged to abut the arm of the actuator to lock the plunger rod in its pre-tensioned state by restricting movement of the arm of the actuator, wherein the holding sleeve is operatively configured to move distally during a medicament delivery operation, thereby allowing the arm of the actuator to be released past an end portion of the holding sleeve causing said release of the plunger rod, and wherein the holding sleeve is operatively configured to be moved proximally during a lockout operation in which the holding sleeve is axially locked by the locking member.

2. The sub-assembly according to claim 1, wherein the locking member is arranged on a portion of the holding sleeve facing the actuator.

3. The sub-assembly according to claim 2, wherein the locking member is an axial rib.

4. The sub-assembly according to claim 1, wherein the arm of the actuator comprises an end hook having a first hook portion arranged to lock the plunger rod in its pre-tensioned state, and a second hook portion arranged opposite to the first hook portion, the second hook portion forming the lockout structure and being arranged to interact with the locking member to axially lock the holding sleeve.

5. The sub-assembly according to claim 1, wherein the locking member is arranged on a portion of the holding sleeve facing the housing.

6. The sub-assembly according to claim 1, wherein the locking member is operatively arranged to snap-fit into the opening of the housing.

7. The sub-assembly according to claim 1, wherein the holding sleeve is biased towards the proximal end of the housing by means of a distal resilient member, and wherein the distal resilient member presses the holding sleeve against the actuator or housing via the locking member in the lockout operation.

8. The sub-assembly according to claim 1, wherein the sub-assembly further comprises a drive spring biasing the plunger rod towards the proximal end of the housing.

9. The sub-assembly according to claim 1, further comprising a delivery member cover arranged in the housing and extending proximally from the proximal end of the housing, the delivery member cover being configured to, during the medicament delivery operation, move linearly relative to the housing from a protracted position to a retracted position in which the delivery member cover is received further in the housing.

10. The sub-assembly according to claim 9, wherein the holding sleeve is fixedly attached to the delivery member cover.

11. A medicament delivery device for expelling medicament from a medicament container via a delivery member, the medicament delivery device comprising a sub-assembly according to claim 1.

* * * * *